United States Patent [19]

Findeisen et al.

[11] Patent Number: 5,209,769
[45] Date of Patent: May 11, 1993

[54] SUBSTITUTED TRIAZOLINONES

[75] Inventors: Kurt Findeisen; Dietmar Kuhnt, both of Leverkusen; Klaus-Helmut Müller, Düsseldorf; Michael Haug, Bergisch Gladbach; Klaus König, Odenthal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 878,149

[22] Filed: May 4, 1992

[30] Foreign Application Priority Data

May 14, 1991 [DE] Fed. Rep. of Germany ....... 4115618

[51] Int. Cl.$^5$ .................. A01N 43/653; C07D 249/12
[52] U.S. Cl. .................. 504/273; 548/263.4; 548/263.8; 504/266; 504/267; 504/268; 504/269; 504/270; 504/271; 504/247; 504/236; 504/237; 504/238; 504/239; 504/242; 504/243; 504/230; 504/253; 504/169
[58] Field of Search ............... 71/92; 548/263.4, 263.8

[56] References Cited

U.S. PATENT DOCUMENTS 5,061,311  10/1991  Findeisen et al. ............... 548/263.8

Primary Examiner—Patricia L. Morris
Attorney, Agent, or Firm—Sprung Horn Kramer & Woods

[57] ABSTRACT

The invention relates to new substituted triazolinones of the general formula (I)

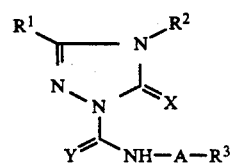

in which $R^1$, $R^2$, $R^3$, A, X and Y have the meanings given in the description, to a plurality of processes for their preparation, and to their use as herbicides.

11 Claims, No Drawings

SUBSTITUTED TRIAZOLINONES

The invention relates to new substituted triazolinones, to a plurality of processes for their preparation and to their use as herbicides.

It has been disclosed that certain substituted triazolinones such as, for example, the compound 4-methyl-3-methylamino-1-(4-phenylbut-2-ylaminocarbonyl)-1,2,4-triazolin-5-one or the compound 4-methyl-3-dimethylamino-1-(4-phenylbut-2-ylaminocarbonyl)-1,2,4-triazolin-5-one or the compound 4-methyl-3-dimethylamino-1-[3-(4-trifluoromethylphenyl)-prop-2-ylaminocarbonyl]-1,2,4-triazolin-5-one have herbicidal properties (compare, for example, EP 283,876 or EP 398,096).

However, the herbicidal activity of these previously known compounds against problem weeds and their compatibility with important crop plants are not entirely satisfactory in all fields of application.

There have been found new substituted triazolinones of the general formula (I),

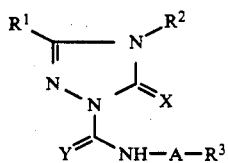  (I)

in which
R$^1$ represents

or a radical —S—R$^6$,
R$^2$ represents alkyl,
R$^3$ represents in each case optionally substituted cycloalkyl, aryl or heterocyclyl,
A represents one of the radicals

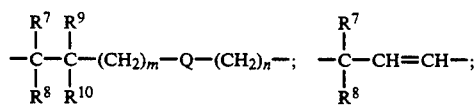

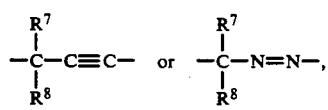

X represents oxygen or sulphur and
Y represents oxygen or sulphur,
where
R$^4$ represents hydrogen or alkyl,
R$^5$ and R$^6$ independently of one another in each case represent alkyl,
R$^7$ represents either hydrogen, cyano or alkyl and
R$^8$, R$^9$ and R$^{10}$ independently of one another in each case represent hydrogen or alkyl or
R$^7$ and R$^8$ together represent a divalent radical of the formula —(CH$_2$)$_p$—,
Q represents oxygen, sulphur, a sulphinyl group, a sulphonyl group or a radical of the formula >N—R$^{11}$,
R$^{11}$ represents hydrogen, alkyl, hydroxyalkyl, alkoxyalkyl, cyanoalkyl or alkanoyl,
m represents a number 0, 1 or 2,
n represents a number 0, 1 or 2 and
p represents a number 2, 3, 4, 5 or 6.

Depending on the nature of the substitutents, the compounds of the formula (I) may, if applicable, exist in the form of geometric and/or optical isomers or isomer mixtures of various compositions. The invention claims the pure isomers as well as the isomer mixtures.

Furthermore, it has been found that the new substituted triazolinones of the general formula (I)

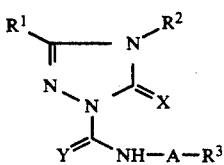  (I)

in which
R$^1$ represents a radical

or a radical —S—R$^6$,
R$^2$ represents alkyl,
R$^3$ represents in each case optionally substituted cycloalkyl, aryl or heterocyclyl,
A represents one of the radicals

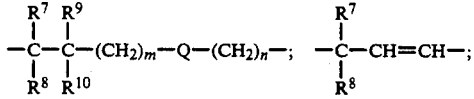

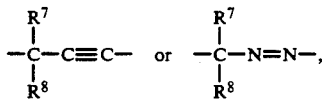

X represents oxygen or sulphur and
Y represents oxygen or sulphur,
where
R$^4$ represents hydrogen or alkyl,
R$^5$ and R$^6$ independently of one another in each case represent alkyl,
R$^7$ represents either hydrogen, cyano or alkyl and
R$^8$, R$^9$ and R$^{10}$ independently of one another in each case represent hydrogen or alkyl or
R$^7$ and R$^8$ together represent a divalent radical of the formula —(CH$_2$)$_p$—,
Q represents oxygen, sulphur, a sulphinyl group, a sulphonyl group or a radical of the formula >N—R$^{11}$,
R$^{11}$ represents hydrogen, alkyl, hydroxyalkyl, alkoxyalkyl, cyanoalkyl or alkanoyl,
m represents a number 0, 1 or 2,
n represents a number 0, 1 or 2 and
p represents a number 2, 3, 4, 5 or 6,
are obtained when a) 1-chloro(thio)carbonyltriazolinones of the formula (II)

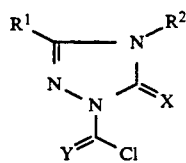

in which
R¹, R², X and Y have the abovementioned meaning, are reacted with amines of the formula (III)

in which
R³ and A have the abovementioned meaning,
if appropriate in the presence of a diluent and if appropriate in the presence of a reaction auxiliary,
or when
b) triazolinones which are unsubstituted in the 1-position, of the formula (IV)

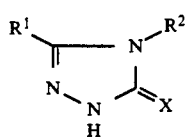

in which
R¹, R² and X have the abovementioned meaning, are reacted with iso(thio)cyanates of the formula (V)

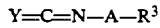

in which
R³, A and Y have the abovementioned meaning,
if appropriate in the presence of a diluent and if appropriate in the presence of a reaction auxiliary.

Finally, it has been found that the new substituted triazolinones of the general formula (I) have herbicidal properties.

Surprisingly, the substituted triazolinones of the general formula (I) according to the invention show a considerably better herbicidal activity against problem weeds and simultaneously an equally good compatibility with important crop plants when compared with the substituted triazolinones which are known from the prior art such as, for example, the compound 4-methyl-3-methylamino-1-(4-phenylbut-2-ylaminocarbonyl)-1,2,4-triazolin-5-one or the compound 4-methyl-3-dimethylamino-1-(4-phenylbut-2-ylaminocarbonyl)-1,2,4-triazolin-5-one or the compound 4-methyl-3-dimethylamino-1-[3-(4-trifluoromethylphenyl)-prop-2-ylaminocarbonyl]-1,2,4-triazolin-5-one, which are similar compounds chemically and from the point of view of their action.

Formula (I) provides a general definition of the substituted triazolinones according to the invention. Preferred compounds of the formula (I) are those in which
R¹ represents a radical

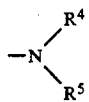

or a radical $-S-R^6$, $R^2$ represents straight-chain or branched alkyl having 1 to 6 carbon atoms, $R^3$ represents cycloalkyl which has 3 to 7 carbon atoms and which is optionally monosubstituted or polysubstituted by identical or different substituents, suitable substituents being: halogen, cyano, in each case straight-chain or branched alkyl having 1 to 4 carbon atoms and in each case straight-chain or branched halogenoalkyl having in each case 1 to 4 carbon atoms and 1 to 9 identical or different halogen atoms;

moreover represents aryl which has 6 or 10 carbon atoms and which is in each case optionally monosubstituted or polysubstituted by identical or different substituents, or represents heteroaryl which has 2 to 9 carbon atoms and 1 to 5 identical or different hetero atoms, in particular nitrogen, oxygen and/or sulphur, suitable substituents in each case being:

halogen, cyano, nitro, in each case straight-chain or branched alkyl, alkoxy or alkylthio having in each case 1 to 4 carbon atoms, in each case straight-chain or branched halogenoalkyl, halogenoalkoxy or halogenoalkylthio having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, dialkylamino having in each case 1 to 4 carbon atoms in the individual straight-chain or branched alkyl moieties, N-alkanoylamino having 1 to 5 carbon atoms in the straight-chain or branched alkanoyl moiety, divalent dioxyalkylene which has 1 to 3 carbon atoms and is optionally monosubstituted or polysubstituted by identical or different halogen substituents, and phenyl, phenoxy, α-naphthyl or β-naphtyl, each of which is optionally monosubstituted or polysubstituted by identical or different substituents from the series comprising halogen and/or in each case straight-chain or branched alkyl or alkoxy each having 1 to 4 carbon atoms, A represents one of the radicals

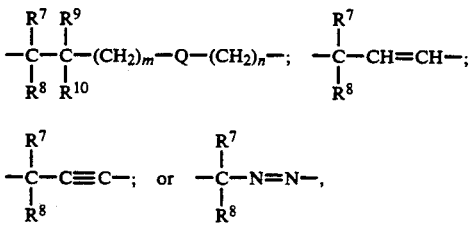

X represents oxygen or sulphur and
Y represents oxygen or sulphur,
where
$R^4$ represents hydrogen or straight-chain or branched alkyl having 1 to 6 carbon atoms, $R^5$ and $R^6$ independently of one another in each case represent straight-chain or branched alkyl having 1 to 6 carbon atoms, $R^7$ represents either hydrogen, cyano or straight-chain or branched alkyl having 1 to 8 carbon atoms and $R^8$, $R^9$ and $R^{10}$ independently of one another in each case represent hydrogen or straight-chain or branched alkyl having 1 to 6 carbon atoms or $R^7$ and $R^8$ together represent a divalent radical of the formula —$(CH_2)_p$—, Q represents oxygen, sulphur, a sulphinyl group, a sulphonyl group or a radical of the formula $>N-R^{11}$, $R^{11}$ represents hydrogen or in each case straight-chain or branched alkyl, hydroxyalkyl, alkoxyalkyl, cyanoalkyl or alkanoyl having in each case 1 to 8 carbon atoms in the individual alkyl moieties, m represents a number 0, 1 or 2, n represents a number 0, 1 or 2 and p represents a number 4, 5 or 6.

Particularly preferred compounds of the formula (I) are those in which $R^1$ represents a radical

$R^2$ represents straight-chain or branched alkyl having 1 to 4 carbon atoms, $R^3$ represents cyclopropyl, cyclobutyl, cyclopentyl or cyclohexyl, each of which is optionally monosubstituted to pentasubstituted by identical or different substituents, suitable substituents in each case being:

fluorine, chlorine, bromine, cyano, methyl, ethyl, n- or i-propyl, chloromethyl, dichloromethyl, trichloromethyl, difluoromethyl or trifluoromethyl; moreover represents phenyl, α-naphthyl, β-naphthyl, indanyl, pyridyl, pyrimidyl, triazinyl, pyridazinyl, pyrazolyl, imidazolyl, triazolyl, thiazolyl, isothiazolyl, benzthiazolyl, oxazolyl, isoxazolyl, benzoxazolyl, benzopyrazolyl, pyrrolyl, furanyl, thienyl, indolyl, benzopyranoyl or quinolyl, each of which is optionally monosubstituted to trisubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl, each of which is optionally monosubstituted to trisubstituted by identical or different substituents from the series comprising fluorine, chlorine, bromine, methyl, ethyl, methoxy and/or ethoxy, A represents one of the radicals

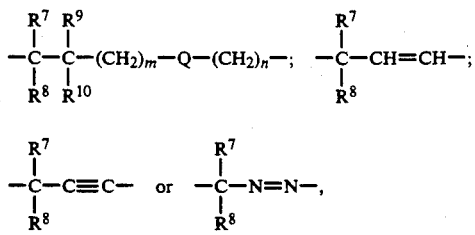

$$-C-C\equiv C- \quad \text{or} \quad -C-N=N-,$$

X represents oxygen or sulphur and

Y represents oxygen or sulphur, where $R^4$ represents hydrogen, methyl or ethyl, $R^5$ represents methyl, ethyl, n- or i-propyl, $R^7$ represents either hydrogen, cyano or straight-chain or branched alkyl having 1 to 6 carbon atoms and $R^8$, $R^9$ and $R^{10}$ independently of one another in each case represent hydrogen or straight-chain or branched alkyl having 1 to 6 carbon atoms, or $R^7$ and $R^8$ together represent a radical of the formula —$(CH_2)_5$—, Q represents oxygen, sulphur or a radical of the formula $>N-R^{11}$, $R^{11}$ represents hydrogen or in each case straight-chain or branched alkyl, hydroxyalkyl, alkoxyalkyl, cyanoalkyl or alkanoyl having in each case 1 to 4 carbon atoms in the individual alkyl moieties, m represents a number 0 or 1 and n represents a number 0 or 1.

Very particularly preferred compounds of the formula (I) are those in which $R^1$ represents N-methylamino, N-ethylamino, N-i-propylamino or dimethylamino, $R^2$ represents methyl, ethyl, n- or i-propyl, n-, i-, s- or t-butyl, $R^3$ represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl, each of which is optionally monosubstituted to trisubstituted by identical or different substituents from the series comprising fluorine, chlorine, bromine, methyl, ethyl, methoxy and/or ethoxy, A represents one of the radicals

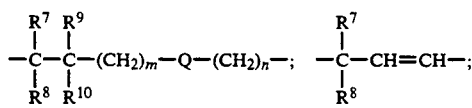
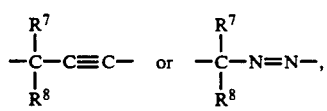

X represents oxygen and
Y represents oxygen,
where
R$^7$ represents either hydrogen, cyano or straight-chain or branched alkyl having 1 to 4 carbon atoms and R$^8$, and R$^9$ and R$^{10}$ independently of one another in each case represent hydrogen or straight-chain or branched alkyl having 1 to 3 carbon atoms, or R$^7$ and R$^8$ together represent a radical of the formula —(CH$_2$)$_5$—, Q represents oxygen, sulphur or a radical of the formula >N—R$^{11}$, R$^{11}$ represents hydrogen or in each case straight-chain or branched alkyl, hydroxyalkyl, alkoxyalkyl, cyanoalkyl or alkanoyl having in each case 1 to 3 carbon atoms in the individual alkyl moieties, m represents a number 0 or 1 and
n represents a number 0 or 1.

Specific reference may be made to the compounds listed in the Preparation Examples.

If, for example, 1-chlorocarbonyl-3-dimethylamino-4-methyl- 1,2,4-triazolin-5-one and 1-(4-methylphenoxy)-3-aminobutane are used as starting substances, the course of the reaction of Process (a) according to the invention can be shown by the following equation:

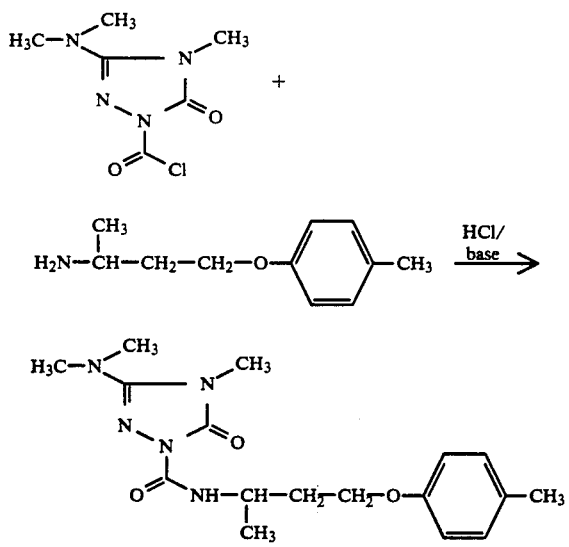

If, for example, 3-diemthylamino-4-methyl-1,2,4-triazolin-5-one and 1-phenylazo-cyclohexylisocyante are used as starting substances, the course of the reaction of Process (b) according to the invention can be shown by the following equation:

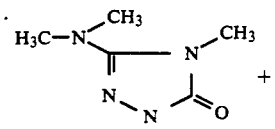

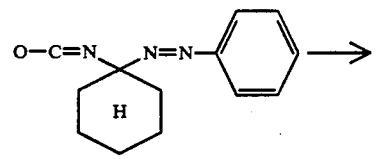

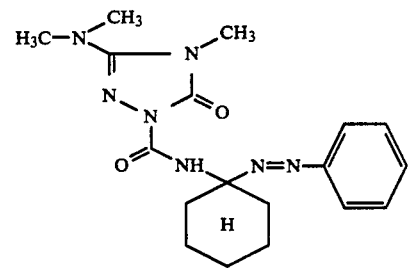

Formula (II) provides a general definition of the 1-chloro(thio)carbonyltriazolinones required as starting substances for carrying out Process (a) according to the invention. In this formula (II), R$^1$, R$^2$, X and Y preferably represent those radicals which have already been mentioned in connection with the description of the compounds of the formula (I) according to the invention as being preferred for these substituents. The 1-chloro(thio)carbonyltriazolinones of the formula (II) are known (compare, for example, EP 283,876).

Formula (III) provides a general definition of the amines furthermore required as starting substances for carrying out Process (a) according to the invention. In this formula (III), R$^3$ and A preferably represent those radicals which have already been mentioned in connection with the description of the compounds of the formula (I) according to the invention as being preferred for these substituents.

The amines of the formula (III) are known or can be obtained in analogy to known processes (compare, for example, EP 273,328; Ind. J. Chem. Sect. B, 24B, 940–947 [1985]; Acta. Pharm. Suec., 20, 349–364 [1983] or CA 100: 174345; An. Quim. 73, 1177–1183 [1977] or CA 89: 129148; Bull. Soc. Chim. Belg. 85, 421–425 [1976]; Tetrahedron Lett. 1976, 2289–2290; Bull. Chem. Soc. Jpn. 60, 609–612 [1987]).

Formula (IV) provides a general definition of the triazolinones which are unsubstituted in the 1-position and which are required as starting materials for carrying out Process (b) according to the invention. In this formula (IV), R$^1$, R$^2$ and X preferably represent those radicals which have already been mentioned in connection with the description of the substances of the formula (I) according to the invention a being preferred for these substituents. The triazolinones which are unsubstituted in the 1-position, of the formula (IV), are known or can be obtained in analogy to known processes (compare, for example, EP 283,876).

Formula (V) provides a general definition of the iso(thio)cyanates furthermore required as starting substances for carrying out Process (b) according to the invention. In this formula (V), R$^2$ and Y preferably represent those radicals which have already been mentioned in connection with the description of the substances of the formula (I) according to the invention as being preferred for these substituents.

The iso(thio)cyanates of the formula (V) are known in some cases (compare, for example, J. med. Chem. 30, 1767–1773 [1987]; J. org. Chem. 35, 47–52 [1970]; Sci. Pharm. 51, 379 [1983]; Synthesis 1984, 315; Synthesis 1990, 803; Angew. Chem. 98, 1111 [1986]; Nouv. J. Chim. 1. 243–254 1977] or CA 87: 151614a) or can be obtained in analogy to known processes (compare, for example, Synthesis 1977, 756; Org. Syntheses Coll. Vol. IV, 521 [1963] or "Organikum" [Laboratory Practical in Organic Chemistry]VEB Deutscher Verlag der Wissenschaften Berlin 1981, p. 703), for example when amines of the formula (III)

$$H_2N-A-R^3 \quad (III)$$

in which

R$^3$ and A have the abovementioned meaning, are reacted with phosgene or thiophosgene, if appropriate in the presence of a diluent such as, for example, toluene or chlorobenzene, at temperatures between $-10°$ C. and $+150°$ C.

Diluents which are suitable for carrying out Process (a) according to the invention are inert organic solvents.

These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or bases such as pyridine.

Process (a) according to the invention is preferably carried out in the presence of a suitable reaction auxiliary. Suitable reaction auxiliaries are all customary inorganic or organic bases. These include, for example, alkaline earth metal hydroxides or alkali metal hydroxides such as sodium hydroxide, calcium hydroxide, potassium hydroxide and also ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU). It is also possible to use a suitable excess of the amine of the formula (III), which is used as reactant, to act simultaneously as a reaction auxiliary.

When carrying out Process (a) according to the invention, the reaction temperatures can be varied within a substantial range. In general, the process is carried out at temperatures between 0° C. and $+150°$ C., preferably at temperatures between $+10°$ C. and $+80°$ C.

For carrying out Process (a) according to the invention, 1.0 to 5.0 moles, preferably 1.0 to 2 moles, of amine of the formula (III) and, if appropriate, 1.0 to 5.0 moles, preferably 1.0 to 2 moles, of base used as reaction auxiliary are generally employed per mole of 1-chloro(thio)-carbonyltriazolinone of the formula (II). The reaction is carried out and the reaction products are worked up and isolated by known processes (compare in this context, for example, EP 283,876 or the Preparation Examples).

Suitable diluents for carrying out Process (b) according to the invention are inert organic solvents. Solvents which are preferably used are those listed in the description of the procedure for Process (a) according to the invention.

If appropriate, Process (b) according to the invention can be carried out in the presence of a suitable basic reaction auxiliary. Suitable basic reaction auxiliaries are all customary inorganic or organic bases. The following are preferably used: tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU). However, an addition of such basic reaction auxiliaries is not essential.

When carrying out Process (b) according to the invention, the reaction temperatures can be varied within a substantial range. In general, the process is carried out at temperatures between 0° C. and $+150°$ C., preferably at temperatures between $+40°$ C. and $+120°$ C.

Process (b) according to the invention is customarily carried out under atmospheric pressure. However, it is also possible to carry out the process under increased or reduced pressure.

For carrying out Process (b) according to the invention, 1.0 to 5.0 moles, preferably 1.0 to 2.5 moles, of iso(thio)cyanate of the formula (V) and, if appropriate, 0.01 to 5.0 moles, preferably 0.1 to 2.5 moles, of base used as reaction auxiliary are generally employed per mole of triazolinone which is unsubstituted in the 1-position, of the formula (IV).

The reaction is carried out and the reaction products are worked up and isolated by known processes (compare in this context, for example, EP 283,876 or the Preparation Examples).

The end products of the formula (I) are purified with the aid of customary processes, for example by column chromatography or by recrystallisation. They are characterised with the aid of the melting point or, in the case of compounds which do not crystallize, with the aid of proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In this context, the active substances according to the invention can be employed with particular success for combating monocotyledon and dicotyledon weeds in monocotyledon cultures such as, for example, wheat or maize. At suitable application rates, the active substances according to the invention also have an insecticidal activity and can be employed, for example, for combating on rice leaf hoppers.

Seepage in the soil, of the compounds of the formula (I), is extremely slow; contamination of the ground water is therefore virtually excluded.

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and 9round natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90 %.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); methyl-6,6-dimethyl-2,4-dioxo-3-[1-(2-propenyloxyamino)-butylidene]cyclohexanecarboxylic acid (ALLOXYDIM); 4-aminobenzenesulphonyl-methyl carbamate (ASULAM); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); N-(3-chlorophenyl)-isopropyl carbamate (CHLORPROPHAM); N,N-dimethyl-N,-(3-chloro-4-methylphenyl)-urea (CHLORTOLURON); exo-1-methyl-4-(1-methylethyl)-2-(2-methylphenyl methoxy)-7-oxabicyclo-(2,2,1)-heptane (CINMETHYLIN); 3,6- dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexyl-thiocarbamate(CYCLOATE);2-[1-(ethoximino)-butyl]-3-hydroxy-5-[tetrahydro-(2H)-thiopyran-3-yl]-2-cyclohexen-1-one (CYCLOXYDIM); 2-[4-(2,4-dichlorophenoxy)phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE);-methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-{[[((4-methoxy-6-methyl-1,3,5-triazin-2-yl)-amino)-carbonyl]-amino]-sulphonyl}-benzoic acid or its methyl ester (METSULFURON); 2-chloro-4-trifluoromethyl-pheny13-ethoxy-4-nitro-phenole ether (OXYFLUORFEN); N-(1-ethylpropyl)- 3,4-dimethyl-2,6-dinitroaniline (PENDIMETHALIN); isopropyl-N-phenyl-carbamate (PROPHAM); 0-(6-chloro-3-phenyl-pyridazin-4-yl) S-octyl thiocarbonate (PYRIDATE); ethyl 2-[4-(6-chloro-quinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE);2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON) or 2,6-dinitro-4-trifluoromethyl-N,N-dipropylaniline (TRIFLURALIN) may also be advantageous. Surprisingly, some mixtures also show synergistic actions.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying; atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES:

EXAMPLE 1

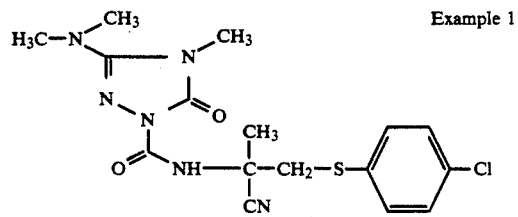

Example 1

A solution of 6.8 g (0.03 mol) of 2-amino-1-(4-chlorophenylthio)-2-cyano-propane and 3.03 g (0.03 mol) of triethylamine in 50 ml of acetonitrile are added dropwise with stirring to 6 g (0.03 mol) of 1-chlorocarbonyl-3-dimethylamino-4-methyl-1,2,4-triazolin-5-one in 150 ml of acetonitrile and, when the addition is complete, stirring of the mixture is continued for 2 hours at room temperature. For working-up, precipitated triethylamine hydrochloride is filtered off, the filtrate is concentrated in vacuo, the residue is taken up in 150 ml of dichloromethane and washed three times with 50 ml portions of water, dried over sodium sulphate and reconcentrated in vacuo. The residue is chromatographed over silica gel (eluent: cyclohexane/ethyl acetate 1:1).

6.8 g (58 % of theory) of 1-[1-(4-chlorophenylthio)-2-cyanoprop-2-yl-aminocarbonyl]-3-dimethylamino-4-methyl- 1,2,4-triazolin-5-one are obtained as an oil.

$^1$H NMR (CDCl$_3$/tetramethylsilane): δ=1.80; 2.85; 3.25; 7.15–7.20; 7.40–7.45; 8.25 ppm.

PREPARATION OF THE STARTING COMPOUND

Example III-1

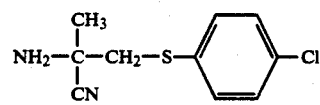

58.6 g (0.862 mol) of 25 % strength ammonia solution and 9.6 g (0.179 mol) of ammonium chloride are added to a solution of 8.79 g (0.179 mol) of sodium cyanide in 13.8 ml of water. 24.7 g (0.123 mol) of 1-(4-chlorophenylthio)-2-propanone (commercially available) are then added, and the mixture is then stirred for 16 hours at 45° C. For working-up, the reaction mixture, which consists of two phases, is taken up in dichloromethane, washed with water, dried over sodium sulphate and concentrated in vacuo.

26.5 g (95 % of theory) of 2-amino-1-(4-chlorophenylthio)-2-propionitrile are obtained as an oil.

IR: ν=2200 (CN), 3250 (NH$_2$)cm$^{-1}$.

EXAMPLE 2

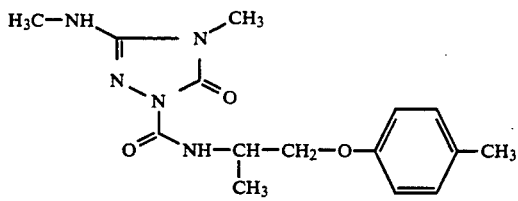

A solution of 3 3 g (0 02 mol) of 2-amino-1-(4-methylphenoxy)-propane (compare, for example, EP 273,328) and 2.02 g (0.02 mol) of triethylamine in 50 ml of acetonitrile are added dropwise with stirring at room temperature to 3.81 g (0.02 mol) of 1-chlorocarbonyl-3-methylamino-4-methyl-1,2,4-triazolin-5-one in 100 ml of acetonitrile, and, when the addition is complete, stirring of the mixture is continued for 2 hours at room temperature. For working-up, precipitated triethylamine hydrochloride is filtered off, the filtrate is concentrated in vacuo, and the residue is stirred with water. The crystals obtained in this process are filtered off, washed with water and dried.

5.6 g (88 % of theory) of 1-[1-(4-methylphenoxy)-prop-2-ylaminocarbonyl]-3-methylamino-4-triazolin-5-one of melting point 96-98° C (decomp.) are obtained.

EXAMPLE 3

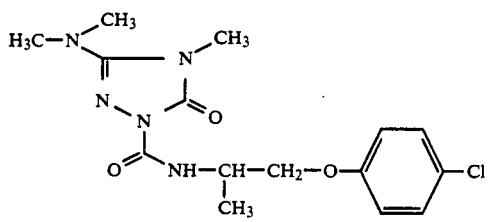

6.33 g (0.03 mol) of 1-(4-chlorophenoxy)-prop-2-yl isocyanate and 3 drops of 1,8-diazabicyclo-[5.4.0]-undec-7-ene (DBU) are added at room temperature with stirring to 4.26 g (0.03 mol) of 3-dimethylamino-4-methyl-1,2,4-triazolin-5-one in 100 ml of acetonitrile, the mixture is subsequently stirred for 5 hours at room temperature and then concentrated in vacuo, and the residue is chromatographed over silica gel (eluent: cyclohexane / ethyl acetate 1:1).

8.9 g (84 % of theory) of 1-[1-(4-chlorophenoxy)-prop-2-ylaminocarbonyl]-3-dimethylamino-4-methyl-1,2,4-triazolin-5-one are obtained as an oil.

$^1$H NMR (CDCl$_3$/tetramethylsilane): δ=2.85; 3.25; 3.95–4.05; 8.10–8.15 ppm.

Preparation of the starting compound

Example V-1

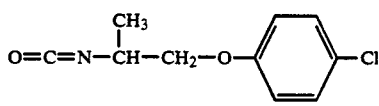

340 g (3.4 mol) of phosgene are passed into 500 ml of chlorobenzene, at 0° C. A solution of 155 g (0.84 mol) of 1-(4-chlorophenoxy)-2-propylamine (compare, for example, Ind. J. Chem. Sect. B, 24B, 940–947 [1985] in 200 ml of chlorobenzene is subsequently added dropwise with stirring at a temperature between 0° C. and 25° C., then, while more phosgene is passed in, the mixture is heated slowly to 90° C. until the solution turns clear, and stirring is continued for a further hour at 90° C. For working-up, the solvent is distilled off, and the residue is distilled in vacuo.

112 g (65 % of theory) of 1-(4-chlorophenoxy)-2-propyl isocyanate of boiling point 120° C at 0.5 mbar are obtained.

IR: ν=2210 cm$^{-1}$ (N=C=O)

The following substituted triazolinones of the general formula (I)

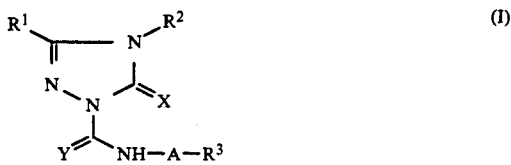

are obtained in a corresponding fashion and following the general preparation instructions:

| Ex. No. | R$^1$ | R$^2$ | R$^3$ | A | X | Y | Physical properties |
|---|---|---|---|---|---|---|---|
| 4 | —N(CH$_3$)CH$_3$ | CH$_3$ | phenyl | —C(CH$_3$)(i-C$_4$H$_9$)—N=N— | O | O | $^1$H NMR*): 0.68–0.7; 1.8; 2.85; 3.3; 9.72 |
| 5 | —N(CH$_3$)CH$_3$ | CH$_3$ | 4-Cl-phenyl | —C(CH$_3$)(CH$_3$)—N=N— | O | O | $^1$H NMR*): 1.81; 2.85; 3.3; 9.45 |
| 6 | —N(CH$_3$)CH$_3$ | CH$_3$ | phenyl | —C(CH$_3$)(CH$_3$)—N=N— | O | O | m.p. 144–145° C. |

-continued

| Ex. No. | R¹ | R² | R³ | A | X | Y | Physical properties |
|---|---|---|---|---|---|---|---|
| 7 | -N(CH₃)₂ | CH₃ | phenyl | 1-(phenylazo)cyclohexyl | O | O | ¹H NMR*): 1.5–2.5; 2.85; 3.3; 8.8 |
| 8 | -N(CH₃)₂ | CH₃ | 4-methoxyphenyl | -CH(CH₃)-CH₂-O- | O | S | ¹H NMR*): 1.45–1.48; 2.85; 3.25; 3.75; 4.95–5.05 |
| 9 | -N(CH₃)₂ | CH₃ | 2,4-dichlorophenyl | -C(CH₃)₂-C≡C- | O | O | ¹H NMR*): 1.81; 2.86; 3.26 |
| 10 | -N(CH₃)₂ | CH₃ | 4-(OCHF₂)phenyl | -C(CH₃)₂-C≡C- | O | O | ¹H NMR*): 1.78; 2.85; 3.25; 6.53 |
| 11 | -N(CH₃)₂ | CH₃ | 4-chlorophenyl | -C(CH₃)₂-C≡C- | O | O | ¹H NMR*): 1.78; 2.86 |
| 12 | -N(CH₃)(C₂H₅) | CH₃ | 4-methoxyphenyl | -CH(CH₃)-CH₂-O- | O | O | ¹H NMR*): 1.17–1.25; 1.37–1.4; 2.85; 3.12–3.2; 3.75 |
| 13 | -N(CH₃)₂ | CH₃ | 3,4-dimethylphenyl | -CH(CH₃)-CH₂-O- | O | O | ¹H NMR*): 1.48–1.5; 2.85; 3.25; 3.93–4.05 |
| 14 | -N(CH₃)₂ | CH₃ | 4-methoxyphenyl | -CH(CH₃)-CH₂-O- | O | O | ¹H NMR*): 1.48–1.5; 2.85; 3.25; 3.75; 3.92–4.05; 8.15–8.2 |
| 15 | -NH-CH₃ | CH₃ | 2-naphthyl | -CH₂-CH₂-NH- | O | O | m.p. 126–128° C. |
| 16 | -NH-CH₃ | CH₃ | 4-chlorophenyl | -C(CH₃)(CN)-CH₂-S- | O | O | m.p. 174–176° C. |
| 17 | -N(CH₃)₂ | CH₃ | 4-chlorophenyl | -C(CH₃)(CN)-CH₂-O- | O | O | m.p. 158–160° C. |
| 18 | -N(CH₃)₂ | CH₃ | 4-chlorophenyl | -C(CH₃)(CN)-CH₂-SO₂- | O | O | m.p. 207–209° C. |

-continued

| Ex. No. | R¹ | R² | R³ | A | X | Y | Physical properties |
|---|---|---|---|---|---|---|---|
| 19 | —NH—CH₃ | CH₃ | 4-methoxyphenyl | —CH(CH₃)—CH₂—O— | O | O | m.p. 100–102° C. |
| 20 | —N(CH₃)₂ | CH₃ | 2,4-dimethylphenyl | —CH(CH₃)—CH₂—O— | O | O | ¹H NMR*): 1.48–1.52; 2.3; 2.85; 4.35–4.45 |
| 21 | —N(CH₃)₂ | CH₃ | 2,5-dimethylphenyl | —CH(CH)—CH—CH₂—O— | O | O | ¹H NMR*): 1.47–1.5; 2.28; 2.85; 3.25; 4.35–4.45; 8.15–8.2 |
| 22 | —N(CH₃)₂ | CH₃ | phenyl | —CH(CH₃)—CH₂—O— | O | O | ¹H NMR*): 1.38–1.4; 2.85; 3.25; 8.1–8.15 |
| 23 | —N(CH₃)₂ | CH₃ | phenyl | —CH₂—CH₂—N(C(=O)C₂H₅)— | O | O | m.p. 128–130° C. |
| 24 | —N(CH₃)₂ | C₂H₅ | 2-methylphenyl | —CH(CH₃)—CH₂—O— | O | O | ¹H NMR*): 1.35–1.43; 2.32; 2.87; 3.68–3.75 |
| 25 | —N(CH₃)₂ | CH₃ | 4-chlorophenyl | —C(CH₃)—CH₂—S— | O | O | ¹H NMR*): 1.35–1.38; 2.85; 3.25; 4.15–4.25 |
| 26 | —N(CH₃)₂ | CH₃ | 2-pyridyl | —C(CH₃)₂—C≡C— | O | O | ¹H NMR*): 1.82; 2.86; 3.26; 8.5–8.58 |
| 27 | —N(CH₃)₂ | CH₃ | 2,2-dimethylchroman-6-yl | —CH(CH₃)—CH₂—O— | O | O | ¹H NMR*): 1.3; 1.35–1.38; 2.85; 3.9–4.05; 4.3–4.45 |
| 28 | —N(CH₃)₂ | CH₃ | phenyl | —CH₂—CH₂—N(C₂H₅)— | O | O | ¹H NMR*): 1.13–1.18; 2.85; 3.25; 8.05–8.1 |
| 29 | —N(CH₃)₂ | CH₃ | 1,1,4-trimethylindan-5-yl | —CH(CH₃)—CH₂—O— | O | O | ¹H NMR*): 1.25–1.28; 2.85; 3.25; 4.0–4.1 |
| 30 | —N(CH₃)₂ | CH₃ | 3-methylphenyl | —CH₂—CH₂—N((CH₂)₂—OH)— | O | O | ¹H NMR*): 1.85–1.95; 2.3; 2.85; 3.25; 3.4–3.5 |

-continued

| Ex. No. | R¹ | R² | R³ | A | X | Y | Physical properties |
|---|---|---|---|---|---|---|---|
| 31 | −N(CH₃)₂ | CH₃ | 2-CH₃, 5-(i-C₃H₇)-phenyl | −CH(CH₃)−CH₂−O− | O | O | $^1$H NMR*): 1.2–1.23; 2.3; 2.85; 3.25; 6.58–6.65 |
| 32 | −N(CH₃)₂ | CH₃ | 2-CH₃, 4-Cl-phenyl | −CH(CH₃)−CH₂−O− | O | O | $^1$H NMR*): 1.48–1.52; 2.32; 2.85; 3.25; 8.15–8.2 |
| 33 | −N(CH₃)₂ | CH₃ | 3,5-(CH₃)₂-phenyl | −CH(CH₃)−CH₂−O− | O | O | $^1$H NMR*): 1.47–1.5; 2.85; 3.25; 3.93–4.05 |
| 34 | −N(CH₃)₂ | CH₃ | 2-chloro-thiazol-5-yl | −C(CH₃)₂−C≡C− | O | O | m.p.: 72° C. |
| 35 | −S−CH₃ | CH₃ | 4-Cl-phenyl | −CH(CH₃)−CH₂−O− | O | O | m.p. 130–131° C. |
| 36 | −N(CH₃)₂ | CH₃ | 3,4-Cl₂-phenyl | −CH₂−CH₂−S−CH₂− | O | O | $^1$H NMR*): 2.6–2.65; 2.85; 3.5–3.6; 7.15–7.45; 8.15–8.25 |
| 37 | −N(CH₃)₂ | CH₃ | phenyl | −CH₂−CH₂−CH₂−O−CH₂− | O | O | $^1$H NMR*): 1.87–1.95; 2.85; 3.25; 4.5; 7.35 |
| 38 | −N(CH₃)₂ | CH₃ | phenyl | −CH₂−CH₂−CH₂−N(CH₃)−CH₂− | O | O | $^1$H NMR*): 1.75–1.85; 2.2; 2.85; 3.25; 3.50 |
| 39 | −N(CH₃)₂ | C₂H₅ | 3,4-Cl₂-phenyl | −CH₂−CH₂−CH₂−O−CH₂− | O | O | $^1$H NMR*): 1.33–1.4; 1.88–2.0; 2.85; 3.5–3.6; 3.65–3.75 |
| 40 | −N(CH₃)₂ | CH₃ | 3-CH₃-phenyl | −CH₂−CH₂−CH₂−NH− | O | O | $^1$H NMR*): 1.83–1.93; 2.28; 2.88; 3.25; 8.0–8.05 |
| 41 | −N(CH₃)₂ | CH₃ | phenyl | −CH₂−CH₂−CH₂−NH− | O | O | $^1$H NMR*): 1.83–1.93; 2.85; 3.25; 3.47–3.53; 6.6–6.7 |

-continued

| Ex. No. | R¹ | R² | R³ | A | X | Y | Physical properties |
|---|---|---|---|---|---|---|---|
| 42 | -N(CH₃)(CH₃) | CH₃ | 2-Cl-phenyl | -CH₂-CH₂-CH₂-NH- | O | O | ¹H NMR*): 1.88-2.0; 2.85; 3.25; 3.5-3.55; 4.5-4.55 |
| 43 | -N(CH₃)(CH₃) | CH₃ | phenyl | -CH₂-CH₂-CH₂-N(i-C₄H₉)-CH₂- | O | O | ¹H NMR*): 0.88-0.9; 1.7-1.8; 2.85; 3.53; 7.17-7.35 |
| 44 | -N(CH₃)(CH₃) | CH₃ | 4-Cl-phenyl | -CH(CH₃)-CH₂-O- | O | O | ¹H NMR*): 1,39-1,42; 2,88; 3,25; 4,35-4,45 |
| 45 | -N(CH₃)(CH₃) | CH₃ | 2,4-F₂-phenyl | -CH(CH₃)-CH₂-O- | O | O | ¹H NMR*): 1,40-1,43; 2,88; 3,28; 4,32-4,42 |
| 46 | -N(CH₃)(CH₃) | CH₃ | 4-(CH₂NH₂)-phenyl | -CH(CH₃)-CH₂-O- | O | O | ¹H NMR*): 1,40-1,42; 2,88; 3,25; 3,95-4,05; 4,5-4,52 |
| 47 | -N(CH₃)(CH₃) | CH₃ | 2,6-(C₂H₅)₂-phenyl | -CH₂-CH₂-NH- | O | O | ¹H NMR*): 1,20-1,26; 2,62-2,70; 2,85; 2,88; 3,58-3,65 |
| 48 | -N(CH₃)(CH₃) | CH₃ | 2-CF₃-4-Cl-phenyl | -CH₂-CH₂-NH- | O | O | Fp. 135-137° C. |
| 49 | -N(CH₃)(CH₃) | CH₃ | 3-Cl-4-CH₃-phenyl | -CH₂-CH₂-NH- | O | O | Fp. 144-146° C. |
| 50 | -N(CH₃)(CH₃) | CH₃ | 3,4-Cl₂-phenyl | -CH₂-CH₂-NH- | O | O | Fp. 146-148° C. |

*) The ¹H NMR spectra were recorded in deuterochloroform (CDCl₃) or hexadeuterodimethyl sulphoxide (DMSO-d₆) with tetramethylsilane (TMS) as the internal standard. The figures denote the chemical shift as δ value in ppm.

USE EXAMPLES

In the use examples which follow, the compounds listed below were employed as comparison substances:

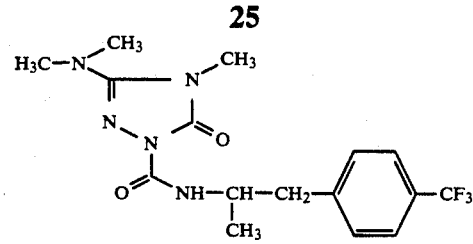

4-methyl-3-dimethylamino-1-[3-(4-trifluoromethyl-phenyl-prop-2-ylaminocarbonyl]-1,2,4-triazolin-5-one

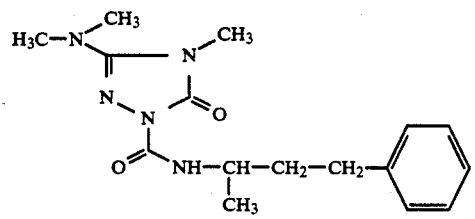

4-methyl-3-dimethylamino-1-(4-phenylbut-2ylaminocarbonyl)-1,2,4-triazolin-5-one

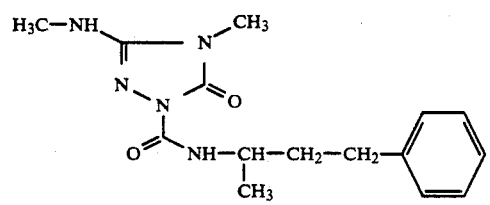

4-methyl-3-methylamino-1-(4-phenylbut-2-ylaminocarbonyl)-1,2,4-triazolin-5-one
(all disclosed in EP 398,096)

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art while having a similar crop plant selectivity is shown, for example, by the compounds of Preparation Examples 1 and 3.

It will be understood that the specification and examples are illustrative but not limitative of the present invention and that other embodiments within the spirit and scope of the invention will suggest themselves to those skilled in the art.

What is claimed is:

1. A substituted triazolinone of the formula (I)

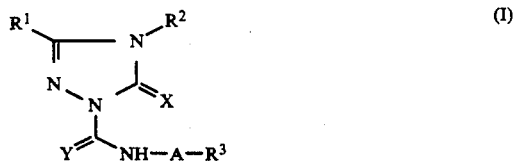

in which
R$^1$ is

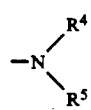

or —S—R$^6$,

R$^2$ is alkyl having 1 to 6 carbon atoms,

R$^3$ is cycloalkyl which has 3 to 7 carbons atoms and which is optionally stubstituted by identical or different substitutents selected from the group consisting of halogen, cyano, and alkyl or halogenoalkyl having 1 to 4 carbon atoms and 1 to 9 identical or different halogen atoms; or is aryl which has 6 to 10 carbon atoms and which is optionally substituted by identical or different substituents selected from the group consisting of halogen, cyano, nitro, alkyl, alkoxy or alkylthio having 1 to 4 carbon atoms, halogenoalkyl, halogenoalkoxy or halogenoalkylthio having 1 to 4 carbon atoms and 1 to 9 identical or different halogen atoms, alkoxycarbonyl or alkoximinoalkyl having 1 to 4 carbon atoms in the individual alkyl moieties, dialkylamino having 1 to 4 carbon atoms in each alkyl moiety, N-alkanoylamino having 1 to 5 carbon atoms in the alkanoyl moiety, divalent dioxyalkylene which has 1 to 3 carbon atoms and is optionally substituted by identical or different halogen substituents, and phenyl, phenoxy, α-naphthyl or β-naphthyl, each of which is optionally substituted by identical or different substituents selected from the group consisting of halogen and alkyl or alkoxy having 1 to 4 carbon atoms, is

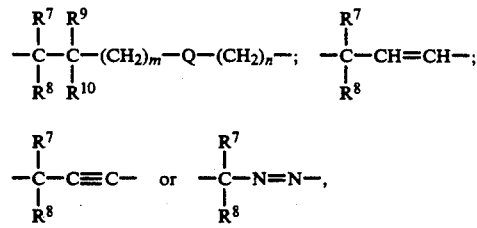

X is oxygen or sulphur and
Y is oxygen or sulphur,
where
R$^4$ is hydrogen or alkyl, having 1 to 6 carbon atoms,
R$^5$ and R$^6$ independently of one another is alkyl, having 1 to 6 carbon atoms, $R^7$ is hydrogen, cyano or alkyl, having 1 to 8 carbon atoms, and $R^8$, $R^9$ and $R^{10}$ independently of one another is hydrogen or alkyl having 1 to 6 carbon atoms or $R^7$ and $R^8$ together are a divalent radical of the formula —$(CH_2)_p$—, Q is oxygen, sulphur, a sulphinyl group, a sulphonyl group or a radical of the formula >N—$R^{11}$, $R^{11}$ is hydrogen or alkyl, hydroxyalkyl, alkoxyalkyl, cyanoalkyl or alkanoyl having 1 to 8 carbon atoms in the individual alkyl moieties m is 0, 1 or 2, n is 0, 1 or 2 and p is 2, 3, 4, 5 or 6.

2. A substituted triazolinone according to claim 1, in which $R^2$ is alkyl having 1 to 6 carbon atoms, $R^4$ is hydrogen or alkyl having 1 to 6 carbon atoms, $R^5$ and $R^6$ independently of one another is alkyl having 1 to 6 carbon atoms, $R^7$ is hydrogen, cyano or alkyl having 1 to 8 carbon atoms and $R^8$, $R^9$ and $R^{10}$ independently of one another is hydrogen or alkyl having 1 to 6 carbon atoms or $R^7$ and $R^8$ together are a divalent radical of the formula —$(CH_2)_p$—, $R^{11}$ is hydrogen or alkyl, hydroxyalkyl, alkoxyalkyl, cyanoalkyl or alkanoyl having 1 to 8 carbon atoms in the individual alkyl moieties, and p is 4, 5 or 6.

3. A substituted triazolinone according to claim 1, which $R^1$ is

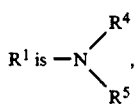

$R^2$ is alkyl having 1 to 4 carbon atoms, $R^3$ is cyclopropyl, cyclobutyl, cyclopentyl or cyclohexyl, each of which is optionally monosubstituted to pentasubstituted by a member selected from the group consisting of fluorine, chlorine, bromine, cyano, methyl, ethyl, n- or i-propyl, chloromethyl, dichloromethyl, trichloromethyl, difluoromethyl and trifluoomethyl; or is phenyl, α-naphthyl or β-naphthyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, and phenyl, phenoxy, α-naphtyl or β-naphthyl, each of which is optionally monosubstituted to trisubstituted by identical or different substituents selected from the group consisting of fluorine, chlorine, fromine, methyl, ethyl, methoxy and ethoxy, $R^4$ is hydrogen, methyl or ethyl, $R^5$ is methyl, ethyl, n- or i-propyl, $R^7$ is hydrogen, cyano or alkyl having 1 to 6 carbon atoms and $R^8$, $R^9$ and $R^{10}$ independently of one another is hydrogen or alkyl having 1 to 6 carbon atoms, or $R^7$ and $R^8$ together are a radical of the formula —$(CH_2)_5$—, $R^{11}$ is hydrogen or alkyl, hydroxyalkyl, alkoxyalkyl, cyanoalkyl or alkanoyl having 1 to 4 carbon atoms in the in individual alkyl moieties, m is 0 or 1 and n is 0 or 1.

4. A substituted triazolinone according to claim 1, in which $R^1$ is N-methylamino, N-ethylamino, N-i-propylamino or dimethylamino, $R^2$ is methyl, ethyl, n- or i-propyl, n-, i-, s- or t-butyl, $R^3$ is phenyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dixoymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinoethyl, and phenyl, phenoxy, α-naphthyl or β-naphthyl, each of which is optionally monosubstituted to trisubstituted by identical or different substituents selected form the group consisting of fluorine, chlorine, bromine, methyl, ethyl, methoxy and ethoxy, X is oxygen and Y is oxygen, where $R^7$ is hydrogen, cyano or alkyl having 1 to 4 carbon atoms, and $R^8$, $R^9$ and $R^{10}$ independently of one another is hydrogen or alkyl having 1 to 3 carbon atoms, or $R^7$ and $R^8$ together are a radical of the formula —$(CH_2)_5$—, $R^{11}$ is hydrogen or alkyl, hydroxyalkyl, alkoxyalkyl, cyanoalkyl or alkanoyl having 1 to 3 carbon atoms in the individual alkyl moieties, m is 0 or 1, and n is 0 or 1.

5. A compound according to claim 1, wherein such compound is 1[1-(4-chlorophenylthio)2-cyanoprop-2-yl-aminocarbonyl]-3-dimethylamino-4-methyl-1,2,4-triazolon-5-one of the formula 6. A compound according to claim 1, wherein such compound is 1-[1-(4-chlorophenoxy)-prop-2yl-aminocarbonyl]-3-dimethylamino-4-methyl-1,2,4-triazolin-5-one of the formula

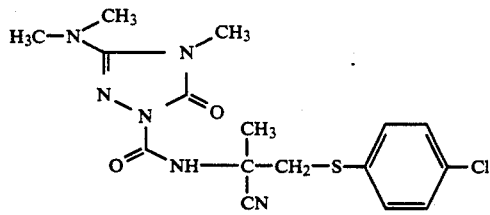

7. A compound according to claim 1, wherein such compound is 1-[1-(4-chlorophenyl)3-methylbutin-2-yl-aminocarbonyl]-3-dimethylamino-4-methyl-1,2,4,-triazolin-5-one of the formula

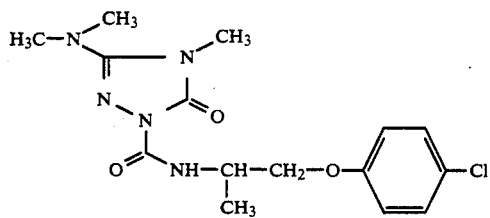

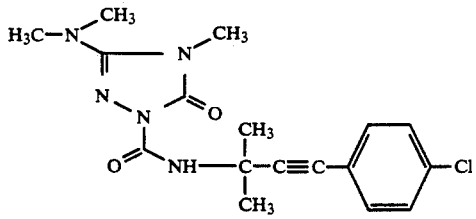

8. A compound according to claim 1, wherein such compound is 1-[1-(N-ethyl-N-phenylamino)-eth-2-yl-aminocarbonyl]-3-dimethylamino-4-methyl-1,2,4-triazolin-5-one of the formula

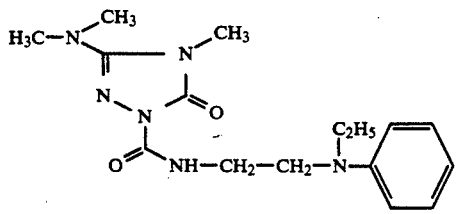

9. A herbicidal composition comprising a herbicidally effective amount of a compound according to claim 1 and a diluent.

10. A method of combating unwanted vegetation which comprises applying to such vegetation or to a Locus from which it is desired to exclude such vegetation a herbicidally effective amount of a compound according to claim 1.

11. A method according to claim 10, wherein such compound is
1-[1-(4-chlorophenylthio)-2-cyanoprop-2-yl-amino-carbonyl]-3-dimethylamino-4-methyl-1,2,4-triazolin-5-one,
1-[1-(4-chlorophenoxy)-prop-2-yl-aminocarbonyl]-3-dimethylamino-4-methyl-1,2,3-triazolin-5-one,
1-[1-(4-chlorophenyl)-3-methylbutin-2-yl-aminocarbonyl]-3-dimethylamino-4-methyl-1,2,4-triazolin-5-one, or
1-[1-(N-ethyl-N-phenylamino)-eth-2-yl-aminocarbonyl]-3-dimethylamino-4-methyl-1,2,4-triazolin-5-one.

* * * * *

UNITED STATES PATENT AND TRADEMARK OFFICE
CERTIFICATE OF CORRECTION

PATENT NO. : 5,209,769
DATED : May 11, 1993
INVENTOR(S) : Findeisen et al.

It is certified that error appears in the above-identified patent and that said Letters Patent is hereby corrected as shown below:

| | |
|---|---|
| Col. 26, line 50 | Before " is " insert -- A -- |
| Col. 26, line 65 | After " alkyl " delete " , " |
| Col. 26, line 67 | After " alkyl " delete " , " |
| Col. 27, line 1 | After " alkyl " delete " , " |
| Col. 27, line 11 | After " moieties " insert -- , -- |
| Col. 27, claim 3 line 3 | Delete " $R^1$ is " |
| Col. 28, line 1 | Delete "fromine " and substitute -- bromine -- |
| Col. 28, line 66 | After " chlorophenylthio) " insert -- - -- |
| Col. 29, line 42 | After " chlorophenyl) " insert -- - -- |
| Col. 30, line 40 | After " 1,2, " delete " 3 " and substitute -- 4 -- |

Signed and Sealed this

Twenty-fifth Day of January, 1994

Attest:

BRUCE LEHMAN

*Attesting Officer*   *Commissioner of Patents and Trademarks*